(12) United States Patent
Hughes et al.

(10) Patent No.: US 6,967,085 B1
(45) Date of Patent: Nov. 22, 2005

(54) FLOCCULATION OF CELL MATERIAL

(75) Inventors: Jonathan Hughes, Brighouse (GB); Steven Weir, Huddersfield (GB); Paul Moran, Ilkley (GB)

(73) Assignee: Ciba Specialty Chemicals Water Treatments Ltd., Bradford (GB)

( * ) Notice: Subject to any disclaimer, the term of this patent is extended or adjusted under 35 U.S.C. 154(b) by 453 days.

(21) Appl. No.: 10/031,835

(22) PCT Filed: Aug. 2, 2000

(86) PCT No.: PCT/EP00/07466

§ 371 (c)(1),
(2), (4) Date: Jan. 22, 2002

(87) PCT Pub. No.: WO01/12778

PCT Pub. Date: Feb. 22, 2001

(30) Foreign Application Priority Data

Aug. 14, 1999 (GB) .................................. 9919187

(51) Int. Cl.[7] .................. C12Q 1/02; C12N 11/02; C12N 11/08; C12N 1/02
(52) U.S. Cl. .................. 435/29; 435/117; 435/180; 435/261
(58) Field of Search .................. 435/243, 261, 435/174, 177, 180, 29

(56) References Cited

U.S. PATENT DOCUMENTS 5,552,316 A    9/1996  Savage .................. 435/261

FOREIGN PATENT DOCUMENTS

EP    0448926    10/1991
WO    98/31749    7/1998

OTHER PUBLICATIONS

Derwent Abstract 1997-488205 [45] for RU 2077594 (1997).
Derwent Abstract 1985-018970 for DD 213690 (1984).
J.-G. Shan et al., Journal of Biotechnology, vol. 49, (1996), pp. 173-178.

Primary Examiner—David M. Naff
(74) Attorney, Agent, or Firm—Shiela A. Loggins

(57) ABSTRACT

A process of flocculating microbial cell material from a suspending medium which contains cell material, comprising adding to the suspending medium a first polymeric material which is cationic and has intrinsic viscosity of not more than 2 dl/g, and subsequently or simultaneously adding to the suspending medium a second polymeric material which is cationic or substantially non-ionic and has intrinsic viscosity of at least 4 dl/g, and allowing the cell material to flocculate.

19 Claims, No Drawings

FLOCCULATION OF CELL MATERIAL

BACKGROUND OF THE INVENTION

1. Field of the Invention

This invention relates to processes of flocculating cell material from suspending media. It is often desired to separate cell material (such as cells and/or cell debris) from a liquid suspending medium containing the cell material. One way of doing this is to flocculate the cell material so that the flocs formed can be separated from the liquid suspending medium. After separation the cell material itself may be further used. Alternatively the cell material can be discarded and the contents of the suspending medium can be used.

2. Description of the Related Art

It has, however, proved difficult to find flocculation systems which give adequate flocculation performance in the suspending media from which cell material must often be separated. In particular, it is often necessary to separate cell material from complex media such as growth medium. It has been found that flocculation using standard flocculants such as polymers is problematic in these environments.

Sitkey et al in Biotechnology Techniques, Vol. 6, no. 1, 49–52 (1992) describe the removal of cells, solids and colloids from fermentation broth. The aim of the separation is to recover extracellular enzymes present in the suspending medium. Sixteen polymeric materials are described for use as flocculating agents. The types of flocculant used are weakly cationic, medium cationic, strong cationic, weakly anionic, medium anionic and non-ionic. However, according to the authors only two polymers gave effective clarification. These were medium anionic polymers Sedipur T1 and Sedipur TF5, available from BASF. The addition of various cationic and non-ionic polymers is described. Each is added as a single dose as the only flocculant and is ineffective in providing clarification of the fermentation broth.

Mukhopadhyay et al in Biotechnology Techniques, vol. 4, no. 2, 121–126 (1990) also attempt to separate suspended solids from a fermentation broth in order to retrieve extracellular enzymes dissolved in the suspending medium. The authors use various different systems in order to improve coagulation or flocculation. The flocculating agents used were glacial acetic acid, calcium chloride, aluminium sulphate and cationic polyacrylamide. Systems of these were also used in which two or more of these agents were added to the suspending medium. In particular, the authors describe systems in which aluminium sulphate and cationic polyacrylamide are used as the two flocculating agents. The amounts of the cationic polyacrylamide used in the exemplified systems were 0.1, 0.3 and 0.5 g/l (100, 300 and 500 ppm). The amount of aluminium sulphate used was always 5.0 g/l (5000 ppm). Although clarification of the fermentation broth was obtained using this system, the authors state that under high shear the flocs formed were disintegrated into smaller particles. This prevents settling. Thus this system can clarify the fermentation broth but does not provide robust flocs. For this reason the processes which can subsequently be used for separating the flocs from the supernatant are limited. In particular the authors advise against even moderate centrifugation.

The publication EP-A448,926 discloses a system for the flocculation of enzyme. Cell material such as cells and cell debris are removed from a suspending medium such as fermentation broth by mechanical means such as centrifugation and the enzyme which remains in the supernatant is flocculated using a particular flocculating agent. The flocculating agent is a blend of a Mannich acrylamide polymer and a diallyl dimethyl ammonium halide polymer. In the system described, it is necessary to remove cell material first from the fermentation broth by mechanical means so that it does not contaminate the later chemically precipitated products.

Weir et al in Biotechnology Techniques, Vol 7, No. 3 (March 1993) pp 199–204, disclose flocculation of cells from fermentation broth using chitosan, a cationic polyelectrolyte reported to be neutral above pH 7.9. The same authors also describe, in Biotechnology Techniques, Vol 8, No. 2 (February 1994) pp 129–132, the use of various anionic polymers as a pretreatment before use of chitosan as a flocculent.

It is known that flocculation of microbial cells in a liquid culture medium by cationic polyelectrolytes aids separation of the cells from the medium. When the medium contains high concentrations of anionic polyelectrolytes as constituents of the medium and/or produced by the cells, the addition of high molecular weight cationic flocculants produces flocs. These flocs will be contaminated with a mixture of concentrated flocculent and polyelectrolyte complex formed from an anionic and cationic polymer (polysalt) and/or precipitate of an anionic and cationic polymer that causes the flocs to stick to processing equipment. An alternative procedure of adding low molecular weight cationic polymer flocculants to bacterial cultures containing high concentrations of anionic polyelectrolytes requires high polymer doses if adequate flocculation is to be achieved because of the formation of anionic and cationic polymer complex and/or precipitates. Moreover, flocs produced using low molecular weight cationic polymer flocculants have been found to be considerably weaker than flocs produced with high molecular weight polymers. Under shear the cells are released from the flocs produced using low molecular weight cationic polymer flocculants and this results in a reduction in separation efficiency.

It would be desirable to be able to provide an efficient system for the separation of cell material from suspending medium such as fermentation broth. It would also be desirable to be able to use a variety of separation methods after flocculation and to be able to provide flocs robust enough to withstand the separation methods and, if necessary, subsequent use.

SUMMARY OF THE INVENTION

According to the invention we provide a process of flocculating cell material from a suspending medium which contains cell material, comprising adding to the suspending medium a first polymeric material which is cationic and which has intrinsic viscosity of not more than 2 dl/g, and subsequently or simultaneously adding to the suspending medium a second cationic polymeric material which is cationic or substantially non-ionic and which has intrinsic viscosity of at least 4 dl/g, and allowing the cell material to flocculate.

We found that the use of the defined first and second polymeric materials in order to flocculate the cell material results in the production of robust flocs suitable for separation under high shear without the need for excessive polymer doses. In particular we found that by pretreating a microbial broth that contains high levels of anionic polyelectrolyte with cationic polymer with an intrinsic viscosity of not more than 2 dl/g and subsequently with polymer flocculant which has an intrinsic viscosity of at least 4. dl/g produces robust flocs containing no sticky concentrated polymer. The total polymer dose is higher than the known method using polymer having an intrinsic viscosity of at least 4 dl/g alone but less than the known method using polymer having an intrinsic viscosity of not more than 2 dl/g alone.

Surprisingly, we also found that the overall polymer dose of the two polymer system of the invention can be reduced by up to 30% when the two polymers are added substantially simultaneously or as a blend. Equally surprising was the finding that the addition of polymer with an intrinsic viscosity of at least 4 dl/g simultaneously or as a blend with polymer having an intrinsic viscosity of not more than 2 dl/g does not produce sticky flocs.

Thus the invention provides flexibility to use various types of separation process without destroying the flocs.

DETAILED DESCRIPTION OF THE INVENTION

In the invention cell material is flocculated from a suspending medium. By cell material we mean cells, cell debris spores and/or biological particulates, in particular cells and/or cell debris. We do not include the flocculation only of cell products such as enzyme or polymer.

The invention may be used to flocculate cell material from various microorganisms.

Thus the invention is of value for flocculating any microbial cell material in a suspending medium. These include bacteria such as *Bacillus subtilis* in suspended media.

The concentration of cell material in the suspending medium is usually at least 0.5 g (dry weight)/l, often at least 2 or 3 g/l and may be up to 100 or 150 g/l.

The suspending medium is often a growth medium so that the cell material is flocculated from fermentation broth. This is a complex medium and contains standard growth medium constituents such as starch (e.g. potato starch), corn meal, corn flour, corn steep liquor, soya flour, maize gluten, yeast extract, molasses distillates, fish meal, peptone and other commercially available lysates. The pH of the suspending medium is not critical but is usually from 3 to 10, often 4 to 9, for instance 6 to 8.

Growth medium tends to contain high levels of anionic material such as anionic polyelectrolytes, either as part of the constituents of the growth medium or as products of the growing cells. The invention is of particular use in such media, since flocculation of cell material from these has been proved to be especially difficult.

In the process of the invention the first and second polymeric materials are added to the suspending medium containing the cell material. The two polymeric materials may be added to the suspending medium sequentially, that is the first cationic polymeric material is added followed by the second cationic polymeric material. When sequential addition is used the first cationic polymeric material is preferably mixed into the suspending medium, prior to the addition of the second cationic polymeric material.

It is preferred that the first and second cationic polymeric materials are added to the suspending medium substantially simultaneously. They can be added separately at the same time, not more than 30 seconds apart. Substantially no mixing of one polymeric material into the suspending medium is carried out before addition of the other.

Preferably they are added as a pre-formed blend. We find that simultaneous addition, especially as a preformed blend, is particularly advantageous in comparison with addition of the two polymeric materials sequentially (ie non-simultaneously). In fact, dosages of both polymeric materials can be reduced with simultaneous addition in comparison with sequential addition and performance maintained.

The polymeric materials may be added to the suspending medium in any suitable form. Suitable addition forms include powder, but aqueous solution is preferred. For instance, if the first and second cationic polymeric materials are added separately each is preferably added as a solution in water of concentration at least 0.05% w/v, and often not more than 1.0% w/v. A suitable concentration in aqueous solution is about 0.1% w/v but can be at much higher concentrations for example in excess of 8.0% w/v and in some cases up to 50.0% w/v.

The amount of active first, cationic, polymeric material added to the suspending medium can be not more than 1000 ppm, preferably not more than 500 ppm, based on the total weight of the suspending medium (including cell material and added polymer).

Often it is not more than 300 or 200 ppm. Good results can be obtained with amounts as low as 150 ppm and below and optimum results can even be obtained with amounts as low as 120 ppm. Generally the amount is at least 50 ppm, often at least 100 ppm. However where high biomass concentrations are to be flocculated very much higher doses may be required for example up to 4000 ppm. Similarly for polymers which have an intrinsic viscosity of at least 4 dl/g higher doses than the ones exemplified above may be required.

The amount of active second polymeric material added to the suspending medium is generally not more than 500 ppm, preferably not more than 250 ppm. It is often below 100 or 80 ppm and optimum results can even be obtained with amounts of 50 ppm or below. Generally the amount is at least 25 ppm.

These amounts of the first and second polymeric materials are suitable for addition separately, (sequentially or simultaneously) and for use of the two polymeric materials as a pre-formed blend. However, simultaneous addition, especially as a pre-formed blend, allows the use of lower amounts than sequential addition. In a pre-formed blend the ratio of the first to the second polymeric material (active polymer, by weight) is preferably from 40:60 to 95:5 first:second polymeric material. More preferably the ratio is from 50:50 to 90:10, most preferably from 60:40 to 80:20. Particularly good results have been obtained with blends in which the ratio of first:second polymeric material is from 65:35 to 75:25, especially about 70:30.

The total amount of active polymer blend added to the suspending medium is generally below 1000 ppm, often below 500 ppm. It can be below 300 or 250 ppm and good results have been obtained with amounts of below 200 ppm. Optimum results can even be achieved with amounts as low as 170 ppm. The total amount of active polymer added to the suspending medium is generally at least 50 ppm, preferably at least 100 ppm.

When the first and second polymeric materials are added as a blend this may be in any suitable form, for instance powder or, preferably, aqueous solution. Total concentration of polymer in aqueous solution is generally at least 0.05% w/v and normally not more than 1% w/v.

We have also devised a novel method for predicting for any particular combination of suspending medium and cell material which dosages of each polymer type will give optimum performance. The method is as follows, 1. A sample of suspending medium is taken. Cell material is separated from the sample of suspending medium by mechanical means, such as batch centrifugation, to provide separated cell material and spent suspending medium.
2. The first polymeric material is added to the spent suspending medium and the increase in absorbance of a well mixed sample measured at 600 nm. The amount of first polymeric material which gives maximum increase in absorbance is noted as Dose 1.
3. The separated cell material is re-suspended in a saline solution having the same volume, ionic strength and pH as the spent suspending medium.
4. The second polymeric material is then added gradually to the re-suspended cell material and the reduction in turbidity measured as an absorbance of a sample measured at 600 nm observed as described hereinafter. The dose of second polymeric material which gives maximum reduction in turbidity is noted as Dose 2.
5. The first and second polymeric materials in the ratio of Dose 1 to Dose 2 are then used to flocculate cell material from the whole suspending medium.

The above method gives an approximation of the optimum ratio of the first and second polymeric materials. In practice however the absolute dose of polymers in the blend form will be lower. In addition the optimum blend ratio may vary from the test method to a small degree in that the low molecular weight fraction may be higher.

The first polymeric material has intrinsic viscosity not more than 2 dl/g. In this specification, intrinsic viscosity (IV) is measured by suspended level viscometer at 25° C. in 1N sodium chloride solution buffered to pH 7. Preferably IV is not more than 1.5 dl/g. Preferably it is at least 0.5 dl/g. It can be up to 1 dl/g or below.

The polymeric material is cationic. It is preferably a synthetic polymeric material and is generally produced by polymerisation of ethylenically unsaturated monomer or monomer blend.

Preferably the first cationic polymeric material has relatively high charge density. In particular it has a theoretical cationic charge density of at least 4 meq/g, usually at least 5 meq/g. Normally theoretical cationic charge density is not more than about 25 meq/g. In this specification the theoretical cationic charge density is the charge density obtained by calculation from the monomeric composition which is intended to be used for forming the polymer.

Preferably the polymer is formed from monomers of which at least 60 wt. %, preferably at least 70 wt. %, are cationic. Cationic monomer content is preferably at least 90 wt. % and can be 100 wt. %.

Suitable cationic monomers include diallyl dialkyl ammonium halides, eg diallyl dimethyl ammonium chloride (DADMAC). Copolymers of this with a minor amount (usually below 30 wt. %, and preferably below 10 wt. %) (meth)acrylamide can be used, although homopolymers are preferred. Homopolymers of dialkylaminoalkyl (meth)acrylate quaternary salt or acid addition salt and homopolymers of dialkylaminoalkyl (meth)acrylamide, optionally as quaternary or acid addition salt, and copolymers of these with small amounts (generally below 30 wt. % and preferably below 10 wt. %) (meth)acrylamide may also be used. Other suitable first cationic polymeric materials include polyethylene imines, polyamines, epichlorhydrin diamine condensation products, dicyandiamide polymers and other conventional low molecular weight cationic coagulant polymers. PolyDADMAC is preferred.

The second polymeric material has intrinsic viscosity at least 6 dl/g. Preferably IV is from 8 to 15 dl/g or 8 to 20 dl/g or higher.

This material may be cationic or substantially non-ionic. Preferably it is cationic. If cationic, the second polymeric material is generally of relatively low cationic charge density. Preferably the theoretical cationic charge density is of the order of 4 meq/g, often about 3 or 2 meq/g. but it can be as low as about 0.1 meq/g, or even about 0.5 meq/g.

The second polymeric material is preferably a synthetic polymer, in particular one formed by polymerisation of ethylenically unsaturated monomer or monomer blend. When the second polymeric material is cationic, the amount of cationic monomer in the blend is usually at least 2 or 3 wt. %. It may be up to 50 wt. %, but is generally not more than 20 wt. %.

Preferred cationic monomers are dialkylaminoalkyl (meth)acrylates as acid addition or, preferably, quaternary salts. Dialkylaminoalkyl (meth)acrylamides, preferably as acid addition or quaternary salts, may be used but preferably the polymer is not a Mannich acrylamide polymer. The alkyl groups may each contain 1 to 4 carbon atoms and the aminoalkyl group may contain 1 to 8 carbon atoms. Particularly preferred are dialkylaminoethyl (meth)acrylates.

These monomers are usually copolymerised with non-ionic monomer such as methacrylamide or, preferably, acrylamide. The second cationic polymeric material can be an amphoteric polymer, due to the inclusion of a lesser amount of anionic monomer, such as acrylic acid or other ethylenically unsaturated carboxylic monomer.

Alternatively the second polymeric material may be substantially non-ionic and may have ionic monomer content below 3 wt. % (based on weight of monomer blend). It may for instance be formed from 100% acrylamide, optionally with a small amount of hydrolysis to form below 3 wt. %, usually below 1 or 2 wt. %, acrylic acid. Other non-ionic monomers include methacrylamide.

The second polymeric material, especially when cationic, can be a wholly water soluble material or it can be in the form of polymers which are crosslinked. The polymer may be made with a small amount of crosslinking agent, eg as described in EP-A-202,780. Preferred polymers of this type have an ionic regain of from 20 to 80% (as defined in EP-A-202,780). Preferably the polymer is a linear polymer.

In the process the first and second polymeric materials are added to the suspending medium and the cell material is allowed to flocculate. Preferably flocculation takes place under agitation. Often this is a continuation of mixing.

When both polymeric materials have been added the suspension is then generally allowed to settle for about 5 to 30 minutes, normally 10 to 20 minutes.

Settling rates are measured by observing the solid interface formed by the flocs of cell material and observing the time this interface takes to travel 1 cm in a standard 12 ml test-tube of diameter 12 mm. In preferred processes the settling rate is at least 3, preferably at least 8 cm/min and in particularly preferred process it is at least 10 cm/min.

Effectiveness of flocculation is measured in terms of the percentage reduction in turbidity (% RT). The % RT is the reduction in absorbance (at 600 nm) of the suspending medium after flocculation in comparison with the absorbance before flocculation. Thus $$\% RT = ((A_1 - A_2) \times 100)/A_1$$

where $A_1$=Absorbance at 600 nm of suspending medium before flocculation and $A_2$=Absorbance at 600 nm of suspending medium after addition of first and second polymeric materials and settlement for 15 minutes.

In the process the % RT can be very high, for instance at least 90 or 95% and can even be at least 98% or substantially 100%.

In the invention we calculate the minimum effective dose (MED) of active polymer. The MED is the lowest active dose of polymer (total of first and second polymeric materials, separately or as a blend) which generates a 90% RT. In the invention the MED can be as low as 200 ppm or below, even as low as 170 ppm or below.

One advantage of the invention lies in the robustness of the flocs which are formed. In the invention we measure floc strength in terms of a floc strength index (FSI). This value represents the strength of the flocs under high shear. The flocs formed after 15 minutes settlement are subjected to high shear. This is defined herein as the shear exerted on 5 ml of suspension in a standard 12 ml test-tube during 30 seconds of vortex mixing produced on the highest setting on a miximatic (Jencons) mixer. The sheared flocs are then allowed to settle for 15 minutes and the % RT of the settled suspension measured. Thus floc strength index=100−(% $RT_A$−% $RT_B$)

where % $RT_A$=% RT after flocculation
and % $RT_B$=% RT after shear.

% RT is always calculated relative to the turbidity of the unflocculated suspending medium.

Preferably the FSI is at least 90%, preferably at least 95% and may even be as high as at least 98%.

Another way of assessing the strength of the flocs is to measure the settlement rate after the shearing test. Preferably settlement rate after shear is at least 2, preferably at least 3 cm/min and is often at least 5 cm/min.

The flocculated cell material is then separated from the clarified suspending medium. Suitable separation methods include centrifugation (batch), semi-continuous continuous, filtration, e.g. vacuum filtration, and any other known separation method.

One advantage of the invention is the improved floc strength which allows the use of various different separation methods, including those which subject the flocs to mechanical agitation and/or shear and would be expected to lead to floc break-up for weaker flocs.

After separation the flocculated cell materials may be used in various processes, e.g. as catalysts. The content of the supernatant may also be used in various processes. If desired, enzyme present in the supernatant may be flocculated from the supernatant.

The invention will now be illustrated by the following examples.

EXAMPLES

In these examples flocculation effectiveness is expressed as % RT measured as described above. Minimum effective dose is measured as described above. Settling rate and floc strength index are also measured as discussed above. The polymers used were as follows:

Polymer 1 polyDADMAC, IV approx 1 dl/g.

Polymer 2 copolymer of 67 wt. % acrylamide and 33 wt. % cationic monomer (dimethylaminoethyl methacrylate quaternised with methyl chloride), IV approx 11 dl/g. In the experiments flocculation is carried out as follows unless otherwise stated. A suspension of Bacillus subtilis with a biomass concentration of 2.7 g (dry weight)/l was used. Aliquots of the medium (4 ml) were placed in 12 ml test tubes and each flocculant polymer or blend added during high intensity agitation on a vortex mixer for about 5 seconds to ensure thorough mixing.

Each polymer or blend was added to the medium as a 0.1% (w/v) solution in water unless otherwise stated.

Example 1

In this example various blends of polymer 1 and polymer 2 were tested to find the optimum ratio for these two polymers on the B. subtilis suspension described above. Blends having ratios of polymer 1:polymer 2 of 40:60, 50:50, 60:40, 65:35 and 70:30 were tested as described above. The 70:30 mix gave the best precipitate, which was wholly particulate. The 65:35 blend also gave an adequate precipitate with some particulate and some stringy nature. For these polymers in this suspension the 40:60, 50:50 and 60:40 blends were not optimum, giving rather "stringy" precipitates.

Example 2

The 70:30 blend found to be optimum in Example 1 was further tested. The MED values for polymer 1 alone, polymer 2 alone and a 70:30 blend of polymer 1 and polymer 2 were found.

The nature of the precipitate was observed, as was the settling rate after addition of the blend.

The % RT after flocculation was also calculated as described above. The flocs were subjected to high shear to obtain the floc strength index as discussed above. After high shear the settling rate was again determined. Results are shown below in Table 1.

TABLE 1

| Polymer | MED/ ppm | Precipitate description | Settling rate cm³/min | Settling rate after high shear cm³/min | Floc strength (FSI) |
|---------|----------|-------------------------|-----------------------|----------------------------------------|---------------------|
| 2       | 130      | stringy                 | 17.6                  | 5.3                                    | 99                  |
| 1       | 229      | particulate             | 1.8                   | 0.3                                    | 86                  |
| Blend   | 166      | particulate             | 10.6                  | 5.3                                    | 99                  |

From these results it can be seen that although polymer 1 alone gave a particulate precipitate, the settling rate was low as was the floc strength, as demonstrated by low FSI and low settling rate after high shear. Polymer 2 alone gave good settling rate and floc strength but a stringy precipitate. The blend gave a particulate precipitate and good settling rate and floc strength. It is also noted that the MED is lower than the MED for polymer 1 and not significantly higher than the MED for polymer 2.

Example 3

In this experiment tests are used to obtain the optimum amount of each of the first and second cationic materials.

A sample of B. subtilis grown to a concentration of 4 g/l in nutrient broth medium was centrifuged at 3000 g for 15 minutes. The supernatant was then recovered and the centrifuged cells were resuspended in the same volume of saline (0.85% [w/w] sodium chloride) solution.

The optimum amount of polymer 1 was obtained by adding solution of polymer 1 continuously to the supernatant until the absorbance at 600 nm reached a maximum. The dose required was 140 ppm.

The optimum dose of polymer 2 was obtained by adding different doses to the suspension of *B. subtilis* suspension in saline until 100% RT was observed. The dose required for this was 50 ppm.

A blend of 140 ppm polymer 1 and 50 ppm polymer 2 was then used to flocculate *B. subtilis* as described above. The % RT after 15 minutes settlement was 100%.

In the following examples the flocculations are carried on in 100 cm$^3$ aliquots in a 250 cm$^3$ beaker agitated with a Lightnin A200 Impellor (4.7 cm diameter) and then the settlement rate is measured in a 100 cm$^3$ measuring cylinder by timing the interval for the flocculated *B. subtilis* mud-line to travel 50 mm.

Polymer 3 is a commercially available cationic polymer [active composition 40% acrylamide and 60% cationic monomer(dimethyl-aminoethyl methacrylate quaternised with methyl chloride)] having an intrinsic viscosity of about 12 dl/g.

Polymer 4 is a commercially available cationic polymer (active composition 20% acrylamide 80% monomer as in polymer 3) having an intrinsic viscosity of 4 dl/g preferably after shear (as described in European Patent 0202780B).

Polymer 1 and 3 or 4 individually or in the blend were added to the medium as a 1% and 0.2% (w/v) solution respectively in water, unless otherwise stated.

Example 4

In this example a dose of polymer 1 is first added to a 4.76 g/l suspension of *B subtilis* grown in 13 g/l nutrient broth (Oxoid) in 2 liter baffled shake flasks at 30° C. for 16 hours. The first dose of polymer 1 used is 210 ppm which is that found to cause maximum precipitation on treatment of the spent medium alone. In a second experiment the dose of polymer 1 used is 290 ppm that is significantly in excess of the dose in the first experiment. The two polymer treated suspension are then divided into aliquots and to each of the aliquoted suspensions (210 and 290 ppm treated), different doses of polymer 3 or polymer 4 are added until a MED of polymer 3 or 4 is observed (95% RT). The results are shown in Table 2.

TABLE 2

Sequential Additions Of Polymers

| Polymer 1 dose (ppm) | 210 | 290 |
|---|---|---|
| Polymer 1 dose (mg/g/drycell) | 44 | 60.9 |
| Polymer 3 MED (ppm) | 175 | 148 |
| Polymer 3 MED (mg/g/drycell) | 36.8 | 31.1 |
| Polymer 4 MED (ppm) | 250 | 200 |
| Polymer 4 MED (mg/g/drycell) | 52.5 | 42.0 |

Results show that a higher dose of polymer 1 results in a reduction in the minimum effective dose of polymer 3 or 4 required.

Example 5

The flocculation of *B Subtilis* at a concentration of 4.76 g(dry cells)/l in spent nutrient broth (Oxoid) by a blend of polymer 1 and polymer 3 at a ratio of 65:35 and blend of polymer 1 and polymer 4 at a ratio of 60:40 was undertaken.

The minimum effective dose of each of the two blends is shown in Table 3.

TABLE 3

| Polymer Blend | MED (ppm) | MED (mg/g [dry cells]) |
|---|---|---|
| Polymer 1: Polymer 3 65:35 | 290 | 60.9 |
| Polymer 1: Polymer 4 60:40 | 414 | 87.0 |

Comparing the total dose of polymer used to flocculate the same B subtilis suspension using polymers added sequentially (e.g. adding the sequential doses of polymer 1 plus polymer 3 in Table 2 of Example 4) and as a blend shows surprisingly that the overall polymer dose is much reduced.

Example 6

Table 4 shows the floc settlement properties and the shear stability of the flocs produced by single polymer 1 addition, sequential polymer 1 followed by polymer 3 or 4 addition and blended polymer 1 and polymer 3 or 4 addition.

As in examples 4 and 5 the suspension to be flocculated is B subtilis at a concentration of 4.76 µl (dry cells) in spent nutrient broth. To test the shear stability of the flocs produced by each method, flocculated suspensions (100 cm$^3$) were sheared in a 250 cm$^3$ beaker using a Triton mixer for 90 seconds (300 rpm stirrer speed, 6.2 cm impeller diameter, 0.5 cm impeller width).

TABLE 4

Settlement rates

| | MED (ppm) | MED (mg/g) | % RT | Settling Rate (cm/min) | Settling rate post-shear (cm/min) | % RT post-shear |
|---|---|---|---|---|---|---|
| Polymer 1 | 700 | 147 | 96.5 | 2.1 | 0.8 | 86.4 |
| Polymer 1 + Polymer 3 | 210 + 221 = 431 | 44.1 + 46.4 = 90.5 | 95.7 | 29.5 | 22.7 | 98.2 |
| Polymer 1 + Polymer 4 | 210 + 280 = 490 | 44.1 + 58.8 = 102.9 | 96.8 | 49.1 | 12.3 | 98.1 |
| 65/35 Polymer 1/Polymer 3 | 320 | 67.2 | 95.7 | 14.4 | 8.4 | 93.3 |
| 65/35 Polymer 1/Polymer 4 | 430 | 90.3 | 96.7 | 18.5 | 3.9 | 92.8 |

Use of polymer 1 alone provides a fine particulate floc suspension with a slow settlement rate and the floc produced had poor shear stability as evidenced by the reduction in % RT after shear. Use of sequentially added polymer 1 and polymer 3 or 4 produces large rapidly settling flocs which are reduced in size (as measured by settlement rate) upon high shear, but which do not erode (as evidenced by high FSI). Polymer blends provide flocs with high settlement rates, which are shear stable at a much reduced overall polymer dose.

What is claimed is:

1. A process of flocculating microbial cell material from a suspending medium which contains cell material, comprising adding to the suspending medium a first polymeric material which is cationic and has intrinsic viscosity of not more than 2 dl/g, and subsequently or simultaneously adding to the suspending medium a second polymeric material which is cationic or substantially non-ionic and has intrinsic viscosity of at least 4 dl/g, and allowing the cell material to flocculate.

2. A process according to claim 1 in which the first polymeric material has a theoretical cationic charge density of at least 5 meq/g.

3. A process according to claim 1 in which the second polymeric material is cationic.

4. A process according to claim 1 in which the second polymeric material has a theoretical cationic charge density of not more than 4 meq/g.

5. A process according to claim 1 in which the second polymeric material is a copolymer of dialkylaminoalkyl (meth)acrylate monomer as a quaternary or acid addition salt with a non-ionic ethylenically unsaturated monomer.

6. A process according to claim 1 in which the first and second polymeric materials are added to the suspending medium simultaneously.

7. A process according to claim 1 in which the first and second polymeric materials are added to the suspending medium as a pre-formed blend.

8. A process according to any preceding claim in which the active dose of the second polymeric material is not more than 500 ppm based on weight of the suspending medium.

9. A process according to claim 1 in which the active dose of the first polymeric material is not more than 1000 ppm based on weight of the suspending medium.

10. A process according to claim 1 in which the first and second polymeric materials are added to the suspending medium as a pre-formed blend and the active dose of the blend is not more than 500 ppm based on weight of the suspending medium.

11. A process according to claim 1 in which the first and second polymeric materials are added to the suspending medium in a ratio of 60:40 to 80:20 first:second polymeric material.

12. A process according to claim 10 in which the first polymeric material is poly diallydimethyl ammonium chloride and the second polymeric material is a copolymer of acrylamide and dimethylaminoethyl acrylate quaternised with methyl chloride.

13. A process according to claim 1 in which the flocculated cell material is separated from the suspending medium and used as a catalyst.

14. A process according to claim 1 in which the active dose of the second polymeric material is not more than 250 ppm based on weight of the suspending medium.

15. A process according to claim 1 in which the active dose of the first polymeric material is not more than 500 ppm based on weight of the suspending medium.

16. A process according to claim 1 in which the first and second polymeric materials are added to the suspending medium as a pre-formed blend and the active dose of the blend is not more than 250 ppm based on weight of the suspending medium.

17. A process according to claim 1 in which the first and second polymeric materials are added to the suspending medium in a ratio of 65:35 to 75:25 first: second polymeric material.

18. A process according to claim 5 in which the second polymeric material is a copolymer of acrylamide and dimethylaminoethyl acrylate quaternized with methyl chloride.

19. The process of claim 1, wherein the amount of said first polymeric material added and the amount of said second polymeric material added is determined by a test method comprising:

i) taking a sample of suspending medium containing suspended cell material and separating cell material from the sample by mechanical means to provide separated cell material and spent suspending meium, ii) adding said first polymeric material to the spent suspending medium and allowing absorbance to increase, iii) repeating the process with further samples of suspending medium and different amounts of said first polymeric material and the amount of said first polymeric material which gives maximum increase in absorbance is the amount of said first polymeric material added, iv) resuspending separated cell material in a saline solution having the same volume, ionic strength and pH as the spent suspending medium, v) adding to the resuspended cell material said second polymeric material and allowing reduction in turbidity to occur, vi) repeating the steps iv) for different amounts of said second polymeric material and the amount of said second polymeric material which gives maximum reduction in turbidity is the amount of said second polymeric material added.

* * * * *